United States Patent
Lange et al.

(10) Patent No.: US 10,660,842 B2
(45) Date of Patent: May 26, 2020

(54) PRODUCT AND METHOD FOR THE TEMPORARY SHAPING OF KERATIN-CONTAINING FIBERS

(71) Applicant: Henkel AG & Co. KGaA, Duesseldorf (DE)

(72) Inventors: Julia Bibiane Lange, Bad Bramstedt (DE); Anna Puls, Winsen (DE); Cyrielle Martinez, Hamburg (DE); Bernd Richters, Hamburg (DE)

(73) Assignee: Henkel AG & Co. KGaA, Duesseldorf (DE)

(*) Notice: Subject to any disclaimer, the term of this patent is extended or adjusted under 35 U.S.C. 154(b) by 0 days.

(21) Appl. No.: 15/556,623

(22) PCT Filed: Jan. 26, 2016

(86) PCT No.: PCT/EP2016/051567
§ 371 (c)(1),
(2) Date: Sep. 8, 2017

(87) PCT Pub. No.: WO2016/142093
PCT Pub. Date: Sep. 15, 2016

(65) Prior Publication Data
US 2018/0055758 A1  Mar. 1, 2018

(30) Foreign Application Priority Data
Mar. 9, 2015  (DE) .................. 10 2015 204 154

(51) Int. Cl.
*A61K 8/81*  (2006.01)
*A61Q 5/06*  (2006.01)
*A61K 8/84*  (2006.01)
*A61K 8/41*  (2006.01)

(52) U.S. Cl.
CPC ............. *A61K 8/8158* (2013.01); *A61K 8/41* (2013.01); *A61K 8/8147* (2013.01); *A61K 8/8152* (2013.01); *A61K 8/8176* (2013.01); *A61K 8/8182* (2013.01); *A61Q 5/06* (2013.01); *A61K 2800/594* (2013.01)

(58) Field of Classification Search
CPC .. A61K 2800/594; A61K 8/41; A61K 8/8147; A61K 8/8152; A61K 8/8158; A61K 8/8176; A61K 8/8182; A61Q 5/06
See application file for complete search history.

(56) References Cited

U.S. PATENT DOCUMENTS

| | | | |
|---|---|---|---|
| 6,319,489 B1 | 11/2001 | Ashton et al. | |
| 2007/0224245 A1* | 9/2007 | Ameer | A61L 27/12 424/426 |
| 2012/0128619 A1 | 5/2012 | Knappe et al. | |

FOREIGN PATENT DOCUMENTS

| WO | 2011057882 A1 | 5/2011 |
| WO | 2013072118 A2 | 5/2013 |
| WO | WO 2013/072118 | * 5/2013 |

OTHER PUBLICATIONS

Ashland (Aquastyle SH-100polymer, Apr. 1, 2014, IDS) (Year: 2014).*
AquaStyleTM SH-100 polymer (https://www.ashland.com/industries/personal-and-home-care/hair-care/aquastyle-sh-100-polymer (Year: 2018).*
EPO, International Search Report and Written Opinion issued in International Application No. PCT/EP2016/051567, dated Mar. 16, 2016.
Ashland, "Ashland Brings Performance and Style to Crystal Clear Gel with AquaStyle: New, Higlhy Functional Polymer for Hair Styling Formulations Offers Consumer-Perceivable Styling Benefits That Stand Up to High Humidity Conditions", Apr. 1, 2014.

* cited by examiner

*Primary Examiner* — Anna R Falkowitz
(74) *Attorney, Agent, or Firm* — Lorenz & Kopf, LLP

(57) ABSTRACT

The disclosure relates to a cosmetic composition for the temporary shaping of hair, containing a combination of an anionic acrylate polymer and an amphoteric polymer. The cosmetic composition provides an extremely good moisture resistance.

14 Claims, No Drawings

PRODUCT AND METHOD FOR THE TEMPORARY SHAPING OF KERATIN-CONTAINING FIBERS

CROSS-REFERENCE TO RELATED APPLICATION

This application is a U.S. National Stage entry under 35 U.S.C. § 371 based on International Application No. PCT/EP2016/051567 filed Jan. 26, 2016 which was published under PCT Article 21(2) and which claims priority to German Application No. 10 2015 204 154.9, filed Mar. 9, 2015, which are all hereby incorporated in their entirety by reference.

TECHNICAL FIELD

The present disclosure pertains to a cosmetic composition for setting hair or for the temporary styling of keratinic fibres, in particular human hair, wherein the composition contains a combination of an anionic acrylate polymer with an amphoteric polymer.

The temporary shaping of hairstyles for a longer period of time of up to several days usually requires the use of firming substances. In this regard, hair treatment agents which serve to temporarily shape the hair play an important role. Appropriate agents for temporary shaping usually contain synthetic polymers and/or waxes as the firming substance. Examples of agents for supporting the temporary styling of keratinic fibres can, for example, be produced as a hairspray, hair wax, hair gel or hair mousse.

The most important property of an agent for the temporary shaping of hair, which will also be referred to below as styling agents, is that the treated fibres in their freshly modelled form—i.e. in which the hair is set—are provided with as strong a hold as possible. This is also known as a strong hold or a firm hold of the styling agent. The hold of the hairstyle is essentially determined by the type and quantity of the firming substance employed, although the other components of the styling agent may also have an influence.

In addition to a firm hold, styling agents must also comply with a whole series of other requirements. These can be broadly classified into properties on the hair, properties of the respective formulation, for example properties of the mousse, the gel or the sprayed aerosol, and properties which relate to handling of the styling agent; the properties on the hair are of particular importance. Moisture resistance, low tack and well-balanced conditioning effects should be mentioned in particular. Furthermore, a styling agent should be able to be used for all types of hair and be gentle on the hair and skin.

In order to meet the various challenges, many synthetic polymers have already been developed as the firming substances and are used in styling agents. The polymers can be classified into cationic, anionic, non-ionic and amphoteric firming polymers. Ideally, when applied to the hair, the polymers produce a polymer film which on the one hand provides the hairstyle with a strong hold, but on the other hand is sufficiently flexible not to break when under stress. If the polymer film is too friable, what are known as film flakes are formed, which are residues which are released when the hair moves and give the impression that the user of the styling agent in question has dandruff. Similar problems occur when waxes are used as the firming substance in styling agents. If the styling agent is a gel or a paste, the polymers should also have thickening properties.

Known amphoteric polymers which are used in hair firming products are based on the monomers N-tert-octylacrylamide, acrylic acid and tert-butylaminoethyl methacrylate. Appropriate polymers and their use in hair styling gels have been described, for example, in international application WO 2011/012464 A2.

Furthermore, hydrophobic modified acrylate copolymers (INCI: acrylates copolymer (and) water) are commercially available; they essentially act as thickening agents. The data sheet for AquaStyle® SH-100 Polymer (Ashland Inc) describes an acrylate copolymer of this type and its use in combination with carbomers. In crystal-clear hair gels, a combination of good initial stiffness, moisture resistance and long-lasting action is described.

One objective as contemplated herein is to provide further suitable polymer combinations which are exemplified by good film-forming and/or firming properties, a very good degree of hold without having to compromise on flexibility and good moisture resistance—in particular perspiration and water resistance—and in addition are suitable for the production of stable viscous as well as stable transparent cosmetic compositions. In particular, currently available styling agents can be further improved because currently, a good combination of stiffness and high humidity curl retention cannot always be sufficiently guaranteed. Thus, one objective as contemplated herein is to provide styling agents of this type which, in addition to the properties mentioned above, in particular provide both good stiffness and also good high humidity curl retention.

BRIEF SUMMARY

A cosmetic composition for the temporary styling of keratinic fibres. The cosmetic composition includes at least one copolymer (a). The at least one copolymer (a) is formed from at least the following monomer units: N-tert-octylacrylamide, acrylic acid, and tert-butylaminoethyl methacrylate. The cosmetic composition further includes at least one anionic acrylate copolymer (b). The at least one anionic acrylate copolymer (b) is formed from at least the following monomer units: at least one (meth)acrylic acid unit, at least one (meth)acrylic acid ethyl ester unit, and at least one (meth)acrylic acid ester unit. The at least one (meth)acrylic acid ester unit differs from the (meth)acrylic acid ethyl ester unit and includes a hydrophobic group as the ester group.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

This is obtained as contemplated herein by a combination of two specific polymers.

The present disclosure provides:
1. A cosmetic composition for the temporary styling of keratinic fibres, which contains:
(a) at least one copolymer (a), which is formed from at least the following monomer units:
(a1) N-tert-octylacrylamide,
(a2) acrylic acid,
(a3) tert-butylaminoethyl methacrylate, and
(b) at least one anionic acrylate copolymer (b), which is formed from at least the following monomer units:
(b1) at least one (meth)acrylic acid unit, (b2) at least one (meth)acrylic acid ethyl ester unit, (b3) at least one (meth)acrylic acid ester unit which differs from the (meth)acrylic acid ethyl ester unit (b2) and contains a hydrophobic group as the ester group.

2. A cosmetic composition in accordance with point 1, wherein the at least one copolymer (a) includes at least about 90% by weight, preferably at least about 95% by weight and in particular at least about 97% by weight of the monomers (a1) N-tert-octylacrylamide, (a2) acrylic acid and (a3) tert-butylaminoethyl methacrylate with respect to its total weight.

3. A cosmetic composition in accordance with one of the preceding points, wherein the copolymer (a) includes at least about 90% by weight, preferably at least about 95% by weight and in particular at least about 97% by weight of the monomers (a1) N-tert-octylacrylamide, (a2) acrylic acid, (a3) tert-butylaminoethyl methacrylate, (a4) methyl methacrylate and (a5) hydroxypropyl methacrylate.

4. A cosmetic composition in accordance with one of the preceding points, wherein the composition contains the copolymer (a) in a proportion of from about 1.0% to about 10% by weight, preferably from about 1.0% to about 8.0% by weight and in particular from about 1.0% to about 5.0% by weight with respect to the total weight of the cosmetic composition.

5. A cosmetic composition in accordance with one of the preceding points, wherein the anionic acrylate copolymer (b) comprises methacrylic acid as the monomer unit (b1) and ethyl acrylate as the monomer unit (b2).

6. A cosmetic composition in accordance with one of the preceding points, wherein the anionic acrylate copolymer (b) comprises a (meth)acrylic acid alkyl ester as the monomer unit (b3).

7. A cosmetic composition in accordance with one of the preceding points, wherein the composition contains the anionic acrylate copolymer (b) in a proportion of from about 0.1% to about 5.0% by weight, preferably from about 1.0% to about 4.0% by weight and in particular from about 1.5% to about 3.0% by weight with respect to the total weight of the cosmetic composition.

8. A cosmetic composition in accordance with one of the preceding points, wherein the anionic acrylate copolymer (b) has a viscosity of from about 60000 to about 120000 cPs for a solids content of 2% by weight in a neutralized aqueous solution at 25° C.

9. A cosmetic composition in accordance with one of the preceding points, wherein the copolymer (a) is a copolymer with the INCI name octylacrylamide/acrylates/butylaminoethyl methacrylate copolymer, in particular Amphomer® (National Starch).

10. A cosmetic composition in accordance with one of the preceding points, wherein the anionic acrylate copolymer (b) is a copolymer with the INCI name acrylates copolymer (and) water, in particular AquaStyle SH-100 (Ashland Inc).

11. A cosmetic composition in accordance with one of the preceding points, wherein the copolymer (a) is a copolymer with the INCI name octylacrylamide/acrylates/butylaminoethyl methacrylate copolymer and the anionic acrylate copolymer (b) is a copolymer with the INCI name acrylates copolymer (and) water.

12. A cosmetic composition in accordance with one of the preceding points, wherein the copolymer is (a) Amphomer® (National Starch) and the anionic acrylate copolymer is (b) AquaStyle® SH-100 (Ashland Inc).

13. A cosmetic composition in accordance with one of the preceding points which contains, with respect to the total weight of the cosmetic composition:

from about 1.0% to about 10% by weight of the copolymer (a), and from about 0.1% to about 15% by weight of the anionic acrylate copolymer (b).

14. A cosmetic composition in accordance with one of the preceding points containing, with respect to the total weight of the cosmetic composition:

from about 1.0% to about 5.0% by weight of the copolymer (a), and from about 5.0% to about 10% by weight of the anionic acrylate copolymer (b).

15. A cosmetic composition in accordance with one of the preceding points, wherein the composition further contains at least one polymer (c) which is different from the copolymers (a) and (b), in particular an anionic or non-ionic polymer (c).

16. A cosmetic composition in accordance with one of the preceding points, wherein with respect to its total weight, it further contains c) from about 1.0% to about 10% by weight of polyvinylpyrrolidone and/or vinylpyrrolidone/vinylacetate-copolymer, preferably polyvinylpyrrolidone.

17. A cosmetic composition in accordance with point 16, wherein the proportion by weight of the polyvinylpyrrolidone and/or vinylpyrrolidone/vinylacetate copolymer (c) with respect to the total weight of the cosmetic composition is from about 2.0% to about 8.5% by weight, preferably from about 3.0% to about 7.0% by weight.

18. A cosmetic composition in accordance with one of the preceding points, wherein the composition contains water in a proportion of from about 50% to about 95% by weight, preferably between about 60% and about 90% by weight and in particular between about 65% and about 85% by weight with respect to the total weight of the cosmetic composition.

19. A cosmetic composition in accordance with one of the preceding points, wherein the composition is a hair gel, hairspray, hair mousse or hair wax, in particular a hair gel.

20. Use of a cosmetic composition in accordance with one of points 1 to 19, for the temporary styling of keratinic fibres.

21. Use of a cosmetic composition in accordance with one of points 1 to 19, to improve the moisture resistance of temporarily shaped keratinic fibres.

22. A method for temporarily shaping keratinic fibres, in particular human hair, in which the cosmetic composition in accordance with one of points 1 to 19 is applied to keratinic fibres.

In the context as contemplated herein, it has surprisingly been shown that by employing a combination of two components which are known per se, which are already used in styling products, an improved moisture resistance can be obtained for the styling products. Other usually required properties of styling products such as high humidity curl retention, stiffness and low tack are retained thereby. A good combination of properties of this type was not expected, even with a knowledge of the individual components, and was surprising. It has been experimentally shown that by employing the combination of the two components, a strong super-additive, i.e. synergistic effect was obtained as regards the moisture resistance, which has been demonstrated by the HHCR test (high humidity curl retention test).

The term "keratinic fibres" as used as contemplated herein encompasses fur, wool and feathers, but in particular human hair.

The essential components of the cosmetic composition as contemplated herein are the amphoteric copolymer (a) and the anionic acrylate copolymer (b) which is different from copolymer (a).

A first essential component of the cosmetic compositions as contemplated herein is copolymer (a). Having regard to the manufacturability, applicability and cosmetic action of the cosmetic compositions as contemplated herein, it has been shown to be advantageous for the proportion by weight of the copolymer (a) with respect to the total weight of the cosmetic composition (a) to be from about 1.0% to about 10% by weight, preferably from about 1.0% to about 8.0% by weight, and in particular from about 1.0% to about 5.0% by weight.

Copolymer (a) is based on the monomers (a1) N-tert-octylacrylamide, (a2) acrylic acid, (a3) tert-butylaminoethyl methacrylate as well as other monomers, as appropriate.

Preferred copolymers (a) preferably consist of at least 90% by weight, preferably at least about 95% by weight and in particular at least about 97% by weight of the monomers (a1) N-tert-octylacrylamide, (a2) acrylic acid, (a3) tert-butylaminoethyl methacrylate. Preferably, the copolymers (a) are obtained using exclusively the monomers N-tert-octylacrylamide, acrylic acid and tert-butylaminoethyl methacrylate.

Particularly preferably, the copolymers (a) are formed from the monomers (a1) N-tert-octylacrylamide, (a2) acrylic acid, (a3) tert-butylaminoethyl methacrylate, (a4) methyl methacrylate and (a5) hydroxypropyl methacrylate. Particularly preferably, the copolymer (a) includes at least about 90% by weight, preferably at least about 95% by weight and in particular at least about 97% by weight of the monomers (a1) N-tert-octylacrylamide, (a2) acrylic acid, (a3) tert-butylaminoethyl methacrylate, (a4) methyl methacrylate and (a5) hydroxypropyl methacrylate.

The copolymers (a) described above are marketed, for example, under the name Amphomer® (INCI name: octylacrylamide/acrylates/butylaminoethyl methacrylate copolymer; CAS number 70801-07-9) by National Starch.

The cosmetic compositions as contemplated herein contain an anionic acrylate copolymer (b) as the second essential component.

The anionic acrylate copolymer (b) is formed from at least the following monomer units: at least one (meth)acrylic acid unit (b1), at least one (meth)acrylic acid ethyl ester unit (b2) and at least one (meth)acrylic acid ester unit (b3), which differs from the (meth)acrylic acid ethyl ester unit (b2) and contains a hydrophobic group as the ester group.

As contemplated herein, the copolymer (b) may be formed out of the following monomer units. In accordance with a preferred embodiment as contemplated herein, the copolymer (b) is, however, formed from the units (b1), (b2) and (b3) only, i.e. it consists of units derived from these monomer units.

The at least one (meth)acrylic acid unit (b1) may be a methacrylic acid unit or acrylic acid unit, wherein a methacrylic acid unit is preferred.

The at least one (meth)acrylic acid ethyl ester unit (b2) may be a methacrylic acid ethyl ester unit or an acrylic acid ethyl ester unit, wherein an acrylic acid ethyl ester unit is preferred.

As contemplated herein, the at least one (meth)acrylic acid ester unit (b3) may be a (meth)acrylic acid alkyl ester unit. The alkyl group of the (meth)acrylic acid alkyl ester unit serves to control the hydrophobic nature of the copolymer. The alkyl group is preferably a linear or branched alkyl group containing from about 2 to about 30 carbon atoms, preferably from about 3 to about 12 carbon atoms. As contemplated herein, the hydrophobic group may also be a hydrophobic group other than an alkyl group, for example an aromatic hydrocarbon ester group. Examples are substituted or unsubstituted phenyl ester groups or substituted or unsubstituted alkylene phenyl ester groups, for example a benzyl ester group.

The viscosity of the anionic acrylate copolymer (b) used in the cosmetic composition is preferably at most from about 60000 to about 120000 cPs for a solids content of 2% by weight and a neutralized solution at 25° C.

Suitable anionic acrylate copolymers (b) are commercially available under the INCI name acrylates copolymer (and) water. Most preferably, the anionic acrylate copolymer is (b) AquaStyle® SH-100 polymer from Ashland, Inc. In the commercially available form, this has a solids content of approximately from about 28% to about 32% by weight and a pH of from about 2.1 to about 4.0.

The cosmetic composition as contemplated herein contains the acrylate copolymer (a) and the copolymer (b) in quantities which are usual and suitable for styling agents, which can be adjusted for special application and packaging.

The composition as contemplated herein may contain the copolymer (a), for example, in a quantity of from about 1.0% to about 10% by weight with respect to the total weight of the composition as contemplated herein. Preferred proportions of copolymer (a) are from about 1.0% to about 8.0% by weight and in particular from about 1.0% to about 5.0% by weight, respectively as the solids content of active substance in the cosmetic composition.

The cosmetic composition as contemplated herein contains the acrylate copolymer (b), with respect to the total weight of the cosmetic composition, for example, in a quantity of from about 0.1% to about 5.0% by weight, preferably from about 1.0% to about 4.0% by weight, more preferably from about 1.5% to about 3.0% by weight, respectively as the solids content of the active substance in the cosmetic composition.

The cosmetic compositions as contemplated herein are also in particular distinguished over alternative cosmetic agents as regards the advantages mentioned above by an improved high humidity curl retention. Regarding the cosmetic properties of the agent in as contemplated herein, a ratio by weight of polymers (a) and (b) in the cosmetic composition of from about 5:1 to about 1:5, preferably from about 3:1 to about 1:3 and in particular from about 2:1 to about 1:2 has been shown to be particularly advantageous.

In a particularly preferred embodiment as contemplated herein, the cosmetic composition contains, as the copolymer (a), the copolymer which is commercially available under the name Amphomer®, and as the acrylate copolymer (b), the commercially available copolymer with the name AquaStyle® SH-100. With this combination, particularly good results are obtained as regards a combination of stiffness and high humidity curl retention. Particularly advantageously, this polymer combination is in the gel form in styling products.

Further generally required properties of styling products such as, for example, moisture resistance and low tack, are also obtained in particular with this combination, particularly when packaged as a hair gel.

The copolymers (a) and (b) are preferably used in the cosmetic composition in the part-neutralized or neutralized form. Preferably, at least one alkanolamine is used for neutralization. The alkanolamines which can be used as the alkalization agent as contemplated herein are preferably selected from primary amines with a $C_2$-$C_6$ alkyl base moiety which carries at least one hydroxyl group. Particularly preferred alkanolamines are selected from the group which is formed by 2-aminoethan-1-ol (monoethanolamine), tris(2-hydroxyethyl)-amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol. As contemplated herein, particularly preferred alkanolamines are selected from the group 2-aminoethan-1-ol, 2-amino-2-methylpropan-1-ol and 2-amino-2-methyl-propan-1,3-diol. 2-amino-2-methylpropanol has been shown to be a particularly suitable neutralization agent in this regard. Preferred cosmetic agents as contemplated herein thus contain 2-amino-2-methylpropanol. The 2-amino-2-methylpropanol is preferably used in the agents as contemplated herein in a quantity which does not exceed the quantity required to neutralize the acrylate copolymers (a) and (b). Preferably, the quantities of 2-amino-2-methylpropanol used in the compositions as contemplated herein are from about 80% to about 100%, particularly preferably from about 90% to about 100% and in particular from about 95% to about 100% of the quantity required to completely neutralize the copolymers (a) and (b). In a preferred embodiment, the quantity by weight of 2-amino-2-methylpropanol with respect to the total weight of the cosmetic agent is from about 0.05% to about 7.0% by weight, preferably from about 0.1% to about 5.0% and in particular from about 0.1% to about 3.0% by weight.

In summary, a preferred cosmetic composition for temporary styling of keratinic fibre contains, with respect to its total weight:
(a) from about 1.0% to about 10% by weight of at least one copolymer (a), which is formed from the following monomer units:
(a1) N-tert-octylacrylamide,
(a2) acrylic acid,
(a3) tert-butylaminoethyl methacrylate, and
(b) from about 0.1 to about 5.0 of at least one anionic acrylate copolymer (b), which is formed from at least the following monomer units:
(b1) at least one methacrylic acid unit,
(b2) at least one acrylic acid ethyl ester unit,
(b3) at least one methacrylic acid ester unit which differs from the acrylic acid ethyl ester unit (b2) and contains a hydrophobic group as the ester group.

Preferably, the cosmetic composition as contemplated herein contains one or more further components which act as thickening agents or gel-forming agents, which are different from the copolymers (a) and (b) and also support the formation of a film. Examples are cationic, anionic, non-ionic or amphoteric polymers. The proportion by weight of these further components with respect to the total weight of the cosmetic composition may be relatively low because of the presence of the components (a) and (b) and, for example, amounts to from about 0.02% to about 3% by weight, preferably from about 0.05% to about 1.5% by weight, more preferably from about 0.2% to about 0.8% by weight.

Examples are acrylamide/ammonium acrylate copolymer, acrylamides/DMAPA acrylates/methoxy PEG methacrylate copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate copolymer, acrylates/t-butylacrylamide copolymer, acrylates/C1-2 succinates/hydroxyacrylates copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/stearyl acrylate/ethylamine oxide methacrylate copolymer, acrylates/VA copolymer, acrylates/VP copolymer, adipic acid/diethylenetriamine copolymer, adipic acid/dimethylaminohydroxypropyl diethylenetriamine copolymer, adipic acid/epoxypropyl diethylenetriamine copolymer, adipic acid/isophthalic acid/neopentyl glycol/trimethylolpropane copolymer, allyl stearate/VA copolymer, aminoethylacrylate phosphate/acrylates copolymer, aminoethylpropanediol-acrylates/acrylamide copolymer, aminoethylpropanediol-AMPD-acrylates/diacetoneacrylamide copolymer, ammonium VA/acrylates copolymer, AMPD-acrylates/diacetoneacrylamide copolymer, AMP-acrylates/allyl methacrylate copolymer, AMP-acrylates/C1-18 alkyl acrylates/C1-8 alkyl acrylamide copolymer, AMP-acrylates/diacetoneacrylamide copolymer, AMP-acrylates/dimethylaminoethyl methacrylate copolymer, bacillus/rice bran extract/soybean extract ferment filtrate, bis-butyloxyamodimethicone/PEG-60 copolymer, butyl acrylate/ethylhexyl methacrylate copolymer, butyl acrylate/hydroxypropyl dimethicone acrylate copolymer, butylated PVP, butyl ester of ethylene/MA copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, dimethicone crosspolymer, diphenyl amodimethicone, ethyl ester of PVM/MA copolymer, hydrolysed wheat protein/PVP crosspolymer, isobutylene/ethylmaleimide/hydroxyethylmaleimide copolymer, isobutylene/MA copolymer, isobutylmethacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, MEA-sulfite, methacrylic acid/sodium acrylamidomethyl propane sulfonate copolymer, methacryloyl ethyl betaine/acrylates copolymer, octylacrylamide/acrylates/butylaminoethyl methacrylate copolymer, PEG/PPG-25/25 dimethicone/acrylates copolymer, PEG-8/SMDI copolymer, polyacrylamide, polyacrylate-6, polybeta-alanine/glutaric acid crosspolymer, polybutylene terephthalate, polyester-1, polyethylacrylate, polyethylene terephthalate, polymethacryloyl ethyl betaine, polypentaerythrityl terephthalate, polyperfluoroperhydrophenanthrene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-24, polyquaternium-27, polyquaternium-28, polyquaternium-29, polyquaternium-30, polyquaternium-31, polyquaternium-32, polyquaternium-33, polyquaternium-34, polyquaternium-35, polyquaternium-36, polyquaternium-37, polyquaternium-39, polyquaternium-45, polyquaternium-46, polyquaternium-47, polyquaternium-48, polyquaternium-49, polyquaternium-50, polyquaternium-55, polyquaternium-56, polysilicone-9, polyurethane-1, polyurethane-6, polyurethane-10, polyvinyl acetate, polyvinyl butyral, polyvinylcaprolactam, polyvinylformamide, polyvinyl imidazolinium acetate, polyvinyl methyl ether, potassium butyl ester of PVM/MA copolymer, potassium ethyl ester of PVM/MA copolymer, PPG-70 polyglyceryl-10 ether, PPG-12/SMDI copolymer, PPG-51/SMDI copolymer, PPG-10 sorbitol, PVM/MA copolymer, PVP, PVP/VA/itaconic acid copolymer, PVP/VA/vinyl propionate copolymer, rhizobian gum, rosin acrylate, shellac, sodium butyl ester of PVM/MA copolymer, sodium ethyl ester of PVM/MA copolymer, sodium polyacrylate, sterculia urens gum, terephthalic acid/isophthalic acid/sodium isophthalic acid sulfonate/glycol copolymer, trimethylolpropane triacrylate, trimethylsiloxysilylcarbamoyl pullulan, VA/crotonates copolymer, VA/crotonates/methacryloxybenzophenone-1 copolymer, VA/crotonates/vinyl neodecanoate copolymer, VA/crotonates/vinyl propionate copolymer, VA/DBM copolymer, VA/vinyl butyl benzoate/crotonates copolymer, vinylamine/vinyl alcohol copolymer, vinyl caprolactam/VP/dimethylaminoethyl methacrylate copolymer, VP/acrylates/lauryl methacrylate copolymer, VP/dimethylaminoethyl methacrylate copolymer, VP/DMAPA acrylates copolymer, VP/hexadecene copolymer, VP/VA copolymer, VP/vinyl caprolactam/DMAPA acrylates copolymer, yeast palmitate and styrene/VP copolymer.

Examples of non-ionic polymers are:
Vinylpyrrolidone/vinyl ester-copolymers such as, for example, those marketed under the trademark Luviskol (BASF). Luviskol VA 64 and Luviskol VA 73, respectively vinylpyrrolidone/vinylacetate copolymers, are preferred non-ionic polymers.
Cellulose ethers such as hydroxypropyl cellulose, hydroxyethyl cellulose and methylhydroxypropyl cellulose, such as those marketed under the trademark Culminalund Benecel (AQUALON).
Shellac.
Polyvinylpyrrolidones, such as those marketed under the trademark Luviskol (BASF).
Siloxanes. These siloxanes may be both water-soluble as well as water-insoluble. Volatile as well as non-volatile siloxanes are suitable; the term "non-volatile siloxanes" should be understood to mean those compounds with a boiling point under normal pressure of over 200° C. Preferred siloxanes are polydialkylsiloxanes such as, for example polydimethylsiloxane, polyalkylaryl siloxanes such as polyphenylmethyl siloxane, for example, ethoxylated polydialkyl siloxanes as well as polydialkyl siloxanes which contain amine and/or hydroxyl groups.
glycosidic substituted silicones.

Furthermore, a homopolyacrylic acid (INCI: carbomer) which is commercially available under the name Carbopol® in a variety of forms, is preferred as the gel-forming component. The carbomer is preferably in a proportion of from about 0.02% to about 3% by weight, preferably from about 0.05% to about 1.5% by weight and more preferably from about 0.2% to about 0.8% by weight with respect to the total weight of the cosmetic composition.

Because of its cosmetic action in combination with the copolymers (a) and (b), as contemplated herein, preferred film-forming polymers are in particular polyvinylpyrrolidones (INCI name: PVP) as well as vinylpyrrolidone/vinylacetate-copolymers (INCI name VP/VA copolymer), wherein the proportion by weight of these polymers is preferably limited to quantities between from about 1.0% and about 10% by weight. Particularly preferred cosmetic compositions as contemplated herein are therefore exemplified in that they further contain from about 1.0% to about 10% by weight of polyvinylpyrrolidone and/or vinylpyrrolidone/vinylacetate copolymer, preferably polyvinylpyrrolidone with respect to their total weight. Particularly preferred cosmetic agents have a proportion by weight of polyvinylpyrrolidone and/or vinylpyrrolidone/vinylacetate copolymer (c) with respect to the total weight of the cosmetic agent of from about 2.0% to about 8.5% by weight, preferably from about 3.0% to about 7.0% by weight.

The cosmetic composition as contemplated herein may contain further normal substances of styling products. Additional care products may in particular be mentioned as the further suitable auxiliary products and additives.

The agent may, for example, contain at least one protein hydrolysate and/or a derivative thereof as the care product. Protein hydrolysates are product mixtures which are obtained by the acidic, basic or enzymatically catalyzed decomposition of proteins. The term "protein hydrolysate" as used in the disclosure should also be understood to include total hydrolysates as well as individual amino acids and their derivatives, as well as mixtures of the various amino acids. The molecular weight of the protein hydrolysates used as contemplated herein is between about 75, the molecular weight of glycine, and about 200000; preferably, the molecular weight is from about 75 to about 50000 and more particularly preferably from about 75 to about 20000 Dalton.

The agent as contemplated herein may also contain at least one vitamin, a provitamin, a vitamin precursor and/or one of its derivatives as the care product. In this regard, as contemplated herein, those vitamins, provitamins and vitamin precursors are preferred which usually are categorized into the groups A, B, C, E, F and H.

Like the addition of glycerine and/or propylene glycol, the addition of panthenol increases the flexibility of the polymer film formed when using the agent as contemplated herein.

The agent as contemplated herein may also contain at least one plant extract as the care product, as well as mono- or oligosaccharides and/or lipids.

Furthermore, oily substances are suitable as the care product. Examples of natural and synthetic cosmetic oily substances include vegetable oils, liquid paraffin oils, isoparaffin oils and synthetic hydrocarbon oils as well as di-n-alkyl ethers containing a total of 12 to 36 carbon atoms, in particular 12 to 24 carbon atoms. Preferred cosmetic agents as contemplated herein contain at least one oily substance, preferably at least one oily substance from the group formed by silicone oils. Particular examples of the silicone oil group include dimethicones, which also includes cyclomethicones, amino-functionalized silicones as well as dimethicone oils. The dimethicones may be both linear and branched, as well as cyclic or cyclic and branched. Particularly suitable silicone oils or silicone gums are dialkyl and alkylaryl siloxanes such as, for example, dimethylpolysiloxane and methylphenylpolysiloxane, as well as their alkoxylated, quaternized and also anionic derivatives. Cyclic and linear polydialkylsiloxanes are preferred, as well as their alkoxylated and/or aminated derivatives, dihydroxypolydimethylsiloxanes and polyphenylalkylsiloxanes.

Ester oils, i.e. esters of $C_6$-$C_{30}$ fatty acids with $C_2$-$C_{30}$ fatty alcohols, preferably monoesters of fatty acids with alcohols containing 2 to 24 C atoms such as, for example, isopropylmyristate (Rilanit® IPM), isononanoic acid-C16-18-alkylester (Cetiol® SN), 2-ethylhexyl palmitate (Cegesoft® 24), stearic acid-2-ethylhexylester (Cetiol® 868), cetyl oleate, glycerine tricaprylate, coco caprylate/caprate (Cetiol® LC), n-butyl stearate, oleyl erucate (Cetiol® J 600), isopropyl palmitate (Rilanit® IPP), oleyl oleate (Cetiol®), lauric acid hexylester (Cetiol® A), di-n-butyladipate (Cetiol® B), myristyl myristate (Cetiol® MM), cetearyl isononanoate (Cetiol® SN), oleic acid decylester (Cetiol® V) are further preferred oily care substances.

Dicarboxylic acid esters, symmetrical, asymmetrical or cyclic esters of carboxylic acids with fatty alcohols, trifatty acid esters of saturated and/or unsaturated linear and/or branched fatty acids with glycerine or fatty acid partial glycerides, which should be understood to include monoglycerides, diglycerides and their technical mixtures, are also suitable as care substances.

Emulsifying agents or surfactants are also preferably contained in the composition as contemplated herein. PEG derivatives of hydrogenated castor oil are preferred, for example those available under the name PEG hydrogenated castor oil, for example PEG-30 hydrogenated castor oil, PEG-33 hydrogenated castor oil, PEG-35 hydrogenated castor oil, PEG-36 hydrogenated castor oil or PEG-40 hydrogenated castor oil. The use of PEG-40 hydrogenated castor oil is preferred in the disclosure. These are preferably employed in a quantity of from about 0.05% to about 1.5% by weight, preferably from about 0.1% to about 1.0% by weight, more preferably from about 0.2% to about 0.8% by weight or from about 0.3% to about 0.6% by weight.

The cosmetic agents as contemplated herein contain the ingredients or substances in a cosmetically acceptable support.

Preferred cosmetically acceptable supports are aqueous, alcoholic or hydroalcoholic media which preferably contain at least 10% by weight of water with respect to the total weight of the agent.

Particularly preferably, the cosmetic support as contemplated herein contains water, in particular in the quantity such that the cosmetic agent, with respect to the total weight of the agent, contains at least about 10% by weight, in particular at least about 20.0% by weight, and most preferably at least about 40% by weight of water. More particularly preferred cosmetic agents exhibit a water content of between about 50% and about 95% by weight, preferably between about 60% and about 90% by weight and in particular between about 65% and about 85% by weight with respect to their total weight.

Particularly for cosmetic purposes, the alcohols employed may be the usually employed lower alcohols containing 1 to 4 carbon atoms such as, for example, ethanol and isopropanol.

Examples of water-soluble solvents as co-solvents are glycerine and/or ethylene glycol and/or 1,2-propylene glycol in a quantity of from about 0 to about 30% by weight with respect to the agent as a whole.

Tabular Overview

The composition of a number of preferred cosmetic agents can be obtained from the following tables (information as the % by weight with respect to the total weight of the cosmetic agent unless indicated otherwise).

|  | Formula 1 | Formula 2 | Formula 3 | Formula 4 | Formula 5 |
| --- | --- | --- | --- | --- | --- |
| Copolymer (a) | 1.0 to 10 | 1.0 to 8.0 | 1.0 to 8.0 | 1.0 to 5.0 | 1.0 to 5.0 |
| Copolymer (b) | 0.1 to 5.0 | 0.1 to 5.0 | 1.0 to 4.0 | 1.0 to 4.0 | 1.5 to 3.0 |
| Misc | to 100 | to 100 | to 100 | to 100 | to 100 |

|  | Formula 1a | Formula 2a | Formula 3a | Formula 4a | Formula 5a |
| --- | --- | --- | --- | --- | --- |
| Copolymer (a): octylacrylamide/ acrylates/ butylaminoethyl methacrylate copolymer | 1.0 to 10 | 1.0 to 8.0 | 1.0 to 8.0 | 1.0 to 5.0 | 1.0 to 5.0 |
| Copolymer (b): acrylates copolymer (and) water | 0.1 to 5.0 | 0.1 to 5.0 | 1.0 to 4.0 | 1.0 to 4.0 | 1.5 to 3.0 |
| Misc | to 100 | to 100 | to 100 | to 100 | to 100 |

|  | Formula 1b | Formula 2b | Formula 3b | Formula 4b | Formula 5b |
| --- | --- | --- | --- | --- | --- |
| Copolymer (a): Amphomer ® (as solids content) | 1.0 to 10 | 1.0 to 8.0 | 1.0 to 8.0 | 1.0 to 5.0 | 1.0 to 5.0 |
| Copolymer (b): AquaStyle ® SH-100 (as solids content) | 0.1 to 5.0 | 0.1 to 5.0 | 1.0 to 4.0 | 1.0 to 4.0 | 1.5 to 3.0 |
| Misc | to 100 | to 100 | to 100 | to 100 | to 100 |

|  | Formula 6 | Formula 7 | Formula 8 | Formula 9 | Formula 10 |
| --- | --- | --- | --- | --- | --- |
| Copolymer (a) | 1.0 to 10 | 1.0 to 8.0 | 1.0 to 8.0 | 1.0 to 5.0 | 1.0 to 5.0 |
| Copolymer (b) | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 6a | Formula 7a | Formula 8a | Formula 9a | Formula 10a |
| --- | --- | --- | --- | --- | --- |
| Copolymer (a): octylacrylamide/ acrylates/ butylaminoethyl methacrylate copolymer | 1.0 to 10 | 1.0 to 8.0 | 1.0 to 8.0 | 1.0 to 5.0 | 1.0 to 5.0 |

-continued

|  | | | | | |
|---|---|---|---|---|---|
| Copolymer (b): acrylates copolymer (and) water | 0.1 to 5.0 | 0.1 to 5.0 | 1.0 to 4.0 | 1.0 to 4.0 | 1.5 to 3.0 |
| Polyvinylpyrrolidone | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 6b | Formula 7b | Formula 8b | Formula 9b | Formula 10b |
|---|---|---|---|---|---|
| Copolymer (a): Amphomer ® (as solids content) | 1.0 to 10 | 1.0 to 8.0 | 1.0 to 8.0 | 1.0 to 5.0 | 1.0 to 5.0 |
| Copolymer (b): AquaStyle ® SH-100 (as solids content) | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 11 | Formula 12 | Formula 13 | Formula 14 | Formula 15 |
|---|---|---|---|---|---|
| Copolymer (a) | 1.0 to 10 | 1.0 to 8.0 | 1.0 to 8.0 | 1.0 to 5.0 | 1.0 to 5.0 |
| Copolymer (b) | 0.1 to 5.0 | 0.1 to 5.0 | 1.0 to 4.0 | 1.0 to 4.0 | 1.5 to 3.0 |
| Vinyl pyrrolidone/vinyl acetate copolymer | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 11a | Formula 12a | Formula 13a | Formula 14a | Formula 15a |
|---|---|---|---|---|---|
| Copolymer (a): octylacrylamide/acrylates/butylaminoethyl methacrylate copolymer | 1.0 to 10 | 1.0 to 8.0 | 1.0 to 8.0 | 1.0 to 5.0 | 1.0 to 5.0 |
| Copolymer (b): acrylates copolymer (and) water | 0.1 to 5.0 | 0.1 to 5.0 | 1.0 to 4.0 | 1.0 to 4.0 | 1.5 to 3.0 |
| Vinyl pyrrolidone/vinyl acetate copolymer | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 11b | Formula 12b | Formula 13b | Formula 14b | Formula 15b |
|---|---|---|---|---|---|
| Copolymer (a): Amphomer ® (as solids content) | 1.0 to 10 | 1.0 to 8.0 | 1.0 to 8.0 | 1.0 to 5.0 | 1.0 to 5.0 |
| Copolymer (b): AquaStyle ® SH-100 (as solids content) | 0.1 to 5.0 | 0.1 to 5.0 | 1.0 to 4.0 | 1.0 to 4.0 | 1.5 to 3.0 |
| Vinyl pyrrolidone/vinyl acetate copolymer | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 16 | Formula 17 | Formula 18 | Formula 19 | Formula 20 |
|---|---|---|---|---|---|
| Copolymer (a) | 1.0 to 10 | 1.0 to 8.0 | 1.0 to 8.0 | 1.0 to 5.0 | 1.0 to 5.0 |
| Copolymer (b) | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Misc | to 100 | to 100 | to 100 | to 100 | to 100 |

|  | Formula 16a | Formula 17a | Formula 18a | Formula 19a | Formula 20a |
|---|---|---|---|---|---|
| Copolymer (a): octylacrylamide/acrylates/butylaminoethyl methacrylate copolymer | 1.0 to 10 | 1.0 to 8.0 | 1.0 to 8.0 | 1.0 to 5.0 | 1.0 to 5.0 |

-continued

|  | | | | | |
|---|---|---|---|---|---|
| Copolymer (b): acrylates copolymer (and) water | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Misc | to 100 | to 100 | to 100 | to 100 | to 100 |

|  | Formula 16b | Formula 17b | Formula 18b | Formula 19b | Formula 20b |
|---|---|---|---|---|---|
| Copolymer (a): Amphomer ® (as solids content) | 1.0 to 10 | 1.0 to 8.0 | 1.0 to 8.0 | 1.0 to 5.0 | 1.0 to 5.0 |
| Copolymer (b): AquaStyle ® SH-100 (as solids content) | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Misc | to 100 | to 100 | to 100 | to 100 | to 100 |

|  | Formula 21 | Formula 22 | Formula 23 | Formula 24 | Formula 25 |
|---|---|---|---|---|---|
| Copolymer (a) | 1.0 to 10 | 1.0 to 8.0 | 1.0 to 8.0 | 1.0 to 5.0 | 1.0 to 5.0 |
| Copolymer (b) | 0.1 to 5.0 | 0.1 to 5.0 | 1.0 to 4.0 | 1.0 to 4.0 | 1.5 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Misc | to 100 | to 100 | to 100 | to 100 | to 100 |

|  | Formula 21a | Formula 22a | Formula 23a | Formula 24a | Formula 25a |
|---|---|---|---|---|---|
| Copolymer (a): octylacrylamide/acrylates/butylaminoethyl methacrylate copolymer | 1.0 to 10 | 1.0 to 8.0 | 1.0 to 8.0 | 1.0 to 5.0 | 1.0 to 5.0 |
| Copolymer (b): acrylates copolymer (and) water | 0.1 to 5.0 | 0.1 to 5.0 | 1.0 to 4.0 | 1.0 to 4.0 | 1.5 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Misc | to 100 | to 100 | to 100 | to 100 | to 100 |

|  | Formula 21b | Formula 22b | Formula 23b | Formula 24b | Formula 25b |
|---|---|---|---|---|---|
| Copolymer (a): Amphomer ® (as solids content) | 1.0 to 10 | 1.0 to 8.0 | 1.0 to 8.0 | 1.0 to 5.0 | 1.0 to 5.0 |
| Copolymer (b): AquaStyle ® SH-100 (as solids content) | 0.1 to 5.0 | 0.1 to 5.0 | 1.0 to 4.0 | 1.0 to 4.0 | 1.5 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Misc | to 100 | to 100 | to 100 | to 100 | to 100 |

|  | Formula 26 | Formula 27 | Formula 28 | Formula 29 | Formula 30 |
|---|---|---|---|---|---|
| Copolymer (a) | 1.0 to 10 | 1.0 to 8.0 | 1.0 to 8.0 | 1.0 to 5.0 | 1.0 to 5.0 |
| Copolymer (b) | 0.1 to 5.0 | 0.1 to 5.0 | 1.0 to 4.0 | 1.0 to 4.0 | 1.5 to 3.0 |
| Water | 50 to 95 | 50 to 95 | 60 to 90 | 60 to 90 | 65 to 85 |
| Misc | to 100 | to 100 | to 100 | to 100 | to 100 |

|  | Formula 26a | Formula 27a | Formula 28a | Formula 29a | Formula 30a |
|---|---|---|---|---|---|
| Copolymer (a): octylacrylamide/acrylates/butylaminoethyl methacrylate copolymer | 1.0 to 10 | 1.0 to 8.0 | 1.0 to 8.0 | 1.0 to 5.0 | 1.0 to 5.0 |
| Copolymer (b): acrylates copolymer (and) water | 0.1 to 5.0 | 0.1 to 5.0 | 1.0 to 4.0 | 1.0 to 4.0 | 1.5 to 3.0 |

-continued

|  | | | | | |
|---|---|---|---|---|---|
| Water | 50 to 95 | 50 to 95 | 60 to 90 | 60 to 90 | 65 to 85 |
| Misc | to 100 | to 100 | to 100 | to 100 | to 100 |

|  | Formula 26b | Formula 27b | Formula 28b | Formula 29b | Formula 30b |
|---|---|---|---|---|---|
| Copolymer (a): Amphomer ® (as solids content) | 1.0 to 10 | 1.0 to 8.0 | 1.0 to 8.0 | 1.0 to 5.0 | 1.0 to 5.0 |
| Copolymer (b): AquaStyle ® SH-100 (as solids content) | 0.1 to 5.0 | 0.1 to 5.0 | 1.0 to 4.0 | 1.0 to 4.0 | 1.5 to 3.0 |
| Water | 50 to 95 | 50 to 95 | 60 to 90 | 60 to 90 | 65 to 85 |
| Misc | to 100 | to 100 | to 100 | to 100 | to 100 |

|  | Formula 31 | Formula 32 | Formula 33 | Formula 34 | Formula 35 |
|---|---|---|---|---|---|
| Copolymer (a) | 1.0 to 10 | 1.0 to 8.0 | 1.0 to 8.0 | 1.0 to 5.0 | 1.0 to 5.0 |
| Copolymer (b) | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 31a | Formula 32a | Formula 33a | Formula 34a | Formula 35a |
|---|---|---|---|---|---|
| Copolymer (a): octylacrylamide/ acrylates/ butylaminoethyl methacrylate copolymer | 1.0 to 10 | 1.0 to 8.0 | 1.0 to 8.0 | 1.0 to 5.0 | 1.0 to 5.0 |
| Copolymer (b): acrylates copolymer (and) water | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 31b | Formula 32b | Formula 33b | Formula 34b | Formula 35b |
|---|---|---|---|---|---|
| Copolymer (a): Amphomer ® (as solids content) | 1.0 to 10 | 1.0 to 8.0 | 1.0 to 8.0 | 1.0 to 5.0 | 1.0 to 5.0 |
| Copolymer (b): AquaStyle ® SH-100 (as solids content) | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 36 | Formula 37 | Formula 38 | Formula 39 | Formula 40 |
|---|---|---|---|---|---|
| Copolymer (a) | 1.0 to 10 | 1.0 to 8.0 | 1.0 to 8.0 | 1.0 to 5.0 | 1.0 to 5.0 |
| Copolymer (b) | 0.1 to 5.0 | 0.1 to 5.0 | 1.0 to 4.0 | 1.0 to 4.0 | 1.5 to 3.0 |
| Vinylpyrrolidone/ vinyl acetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 36a | Formula 37a | Formula 38a | Formula 39a | Formula 40a |
|---|---|---|---|---|---|
| Copolymer (a): octylacrylamide/ acrylates/ butylaminoethyl methacrylate copolymer | 1.0 to 10 | 1.0 to 8.0 | 1.0 to 8.0 | 1.0 to 5.0 | 1.0 to 5.0 |
| Copolymer (b): acrylates copolymer (and) water | 0.1 to 5.0 | 0.1 to 5.0 | 1.0 to 4.0 | 1.0 to 4.0 | 1.5 to 3.0 |

-continued

| | | | | | |
|---|---|---|---|---|---|
| Vinylpyrrolidone/ vinyl acetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

| | Formula 36b | Formula 37b | Formula 38b | Formula 39b | Formula 40b |
|---|---|---|---|---|---|
| Copolymer (a): Amphomer ® (as solids content) | 1.0 to 10 | 1.0 to 8.0 | 1.0 to 8.0 | 1.0 to 5.0 | 1.0 to 5.0 |
| Copolymer (b): AquaStyle ® SH-100 (as solids content) | 0.1 to 5.0 | 0.1 to 5.0 | 1.0 to 4.0 | 1.0 to 4.0 | 1.5 to 3.0 |
| Vinylpyrrolidone/ vinyl acetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

| | Formula 41 | Formula 42 | Formula 43 | Formula 44 | Formula 45 |
|---|---|---|---|---|---|
| Copolymer (a) | 1.0 to 10 | 1.0 to 8.0 | 1.0 to 8.0 | 1.0 to 5.0 | 1.0 to 5.0 |
| Copolymer (b) | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | to 100 | to 100 | to 100 | to 100 | to 100 |

| | Formula 41a | Formula 42a | Formula 43a | Formula 44a | Formula 45a |
|---|---|---|---|---|---|
| Copolymer (a): octylacrylamide/ acrylates/ butylaminoethyl methacrylate copolymer | 1.0 to 10 | 1.0 to 8.0 | 1.0 to 8.0 | 1.0 to 5.0 | 1.0 to 5.0 |
| Copolymer (b): acrylates copolymer (and) water | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | to 100 | to 100 | to 100 | to 100 | to 100 |

| | Formula 41b | Formula 42b | Formula 43b | Formula 44b | Formula 45b |
|---|---|---|---|---|---|
| Copolymer (a): Amphomer ® (as solids content) | 1.0 to 10 | 1.0 to 8.0 | 1.0 to 8.0 | 1.0 to 5.0 | 1.0 to 5.0 |
| Copolymer (b): AquaStyle ® SH-100 (as solids content) | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | to 100 | to 100 | to 100 | to 100 | to 100 |

| | Formula 46 | Formula 47 | Formula 48 | Formula 49 | Formula 50 |
|---|---|---|---|---|---|
| Copolymer (a) | 1.0 to 10 | 1.0 to 8.0 | 1.0 to 8.0 | 1.0 to 5.0 | 1.0 to 5.0 |
| Copolymer (b) | 0.1 to 5.0 | 0.1 to 5.0 | 1.0 to 4.0 | 1.0 to 4.0 | 1.5 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | to 100 | to 100 | to 100 | to 100 | to 100 |

| | Formula 46a | Formula 47a | Formula 48a | Formula 49a | Formula 50a |
|---|---|---|---|---|---|
| Copolymer (a): octylacrylamide/ acrylates/ butylaminoethyl methacrylate copolymer | 1.0 to 10 | 1.0 to 8.0 | 1.0 to 8.0 | 1.0 to 5.0 | 1.0 to 5.0 |

-continued

| | | | | | |
|---|---|---|---|---|---|
| Copolymer (b): acrylates copolymer (and) water | 0.1 to 5.0 | 0.1 to 5.0 | 1.0 to 4.0 | 1.0 to 4.0 | 1.5 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | to 100 | to 100 | to 100 | to 100 | to 100 |

| | Formula 46b | Formula 47b | Formula 48b | Formula 49b | Formula 50b |
|---|---|---|---|---|---|
| Copolymer (a): Amphomer ® (as solids content) | 1.0 to 10 | 1.0 to 8.0 | 1.0 to 8.0 | 1.0 to 5.0 | 1.0 to 5.0 |
| Copolymer (b): AquaStyle ® SH-100 (as solids content) | 0.1 to 5.0 | 0.1 to 5.0 | 1.0 to 4.0 | 1.0 to 4.0 | 1.5 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | to 100 | to 100 | to 100 | to 100 | to 100 |

The term "misc" as used as contemplated herein should be understood to mean a cosmetic support, in particular (unless separately mentioned) water and, if appropriate, other usual components of styling products.

The cosmetic composition as contemplated herein may be packaged in the usual forms for packaging temporary hair styling products, for example as a hair gel, hairspray, hair mousse or hair wax. Packaging as a hair gel is preferred.

Both hair mousses and hairsprays require the presence of propellants. As contemplated herein, however, preferably, no or only small quantities of hydrocarbons should be used in this regard. Propane, propane/butane mixtures and dimethyl ether are particularly suitable propellants for use in the disclosure.

The present disclosure also concerns the use of cosmetic compositions as contemplated herein for the temporary styling of keratinic fibres, in particular human hair, as well as a method for temporary shaping of keratinic fibres, in particular human hair, in which the cosmetic composition as contemplated herein is applied to keratinic fibres.

The use of a cosmetic composition as contemplated herein for improving the moisture resistance of temporarily shaped keratinic fibres constitutes a further object of this disclosure.

EXAMPLES

The following hair gels were produced:

| Component/raw material | INCI name or chemical description | V1 | V2 | E1 |
|---|---|---|---|---|
| Amphomer ®[1] | Octylacrylamide/acrylates/butylaminoethyl methacrylate copolymer | 5.0 | — | 2.5 |
| AquaStyle SH-100[2] | Acrylates copolymer (and) water | — | 16.5 | 8.25 |
| AMP-ULTRA PC 2000 | Aminomethyl propanol | 0.9 | 0.3 | 0.6 |
| Water | | 94.1 | 83.2 | 88.65 |
| Total | | 100 | 100 | 100 |

[1]100% by weight of active substance
[2]30% by weight of active substance in water The quantities in the table are given as a % by weight of the respective raw material, with respect to the total composition. The polymer content in each of the compositions V1, V2 and E2 was 5.0% by weight.

For the styling agents obtained, the moisture resistance was determined for clean Kerling hair strands using a HHCR test (high humidity curl retention test: 6 h) (mean value in each case determined for 5 hair strands):

| | V1 | V2 | E1 |
|---|---|---|---|
| HHCR | 64% | 72% | 84% |

The polymer combination E1 as contemplated herein thus exhibited a substantially super-additive, synergistic effect as regards the moisture resistance.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:
1. A cosmetic composition for the temporary styling of keratinic fibres, which consists of:
    a copolymer (a), which is formed from at least the following monomer units;
        N-tert-octylacrylamide,
        acrylic acid, and
        tert-butylaminoethyl methacrylate;
    an anionic acrylate copolymer (b), which is formed from at least the following monomer units;
        at least one methacrylic acid unit,
        at least one ethyl acrylate unit, and at least one (meth)acrylic acid alkyl ester;
at least one alkanolamines; and
water in a proportion of from about 50 to about 95% by weight with respect to the total weight of the cosmetic composition.

2. The cosmetic composition as claimed in claim 1, wherein the composition comprises the copolymer (a) in a proportion of from about 1.0% to about 5.0% by weight with respect to the total weight of the cosmetic composition.

3. The cosmetic composition as claimed in claim 2, wherein the composition comprises the anionic acrylate copolymer (b) in a proportion of from about 1.5 to about 3.0 by weight with respect to the total weight of the cosmetic composition.

4. The cosmetic composition as claimed in claim 1, wherein the composition is a hair gel, hairspray, hair mousse or hair wax.

5. The cosmetic composition as claimed in claim 1, wherein the cosmetic composition is utilized for the temporary styling of keratinic fibres.

6. A method for temporarily shaping keratinic fibres, the method comprising applying the cosmetic composition as claimed in claim 1 to keratinic fibres.

7. The cosmetic composition as claimed in claim 1, wherein the anionic acrylate copolymer (b) has a viscosity of from about 60000 to about 120000 cPs for a solids content of 2% by weight in a neutralized aqueous solution at 25° C.

8. The cosmetic composition as claimed in claim 1, wherein the copolymer (a) is a copolymer with the INCI name octylacrylamide/acrylates/butylaminoethyl methacrylate copolymer.

9. The cosmetic composition as claimed in claim 1, wherein the anionic acrylate copolymer (b) is a copolymer with the INCI name acrylates copolymer (and) water.

10. The cosmetic composition according to claim 1, wherein the at least one alkanolamine comprises 2-aminoethan-1-ol, 2-amino-2-methylpropan-1-ol, 2-amino-2-methyl-propan-1,3-di ol, or combinations thereof.

11. The cosmetic composition of claim 1, wherein the copolymer (a) includes at least 97% by weight of the monomers (a1) N-tert-octylacrylamide, (a2) acrylic acid, (a3) tert-butylaminoethyl methacrylate, (a4) methyl methacrylate and (a5) hydroxypropyl methacrylate.

12. The cosmetic composition of claim 11, wherein the composition comprises the copolymer (a) in a proportion of from about 1.0% to about 5.0% by weight with respect to the total weight of the cosmetic composition.

13. The cosmetic composition of claim 12, wherein the composition comprises the copolymer (b) in a proportion of from about 1.5 to about 3.0 by weight with respect to the total weight of the cosmetic composition.

14. The cosmetic composition of claim 12, wherein the composition comprises the copolymer (a) and the copolymer (b) in a weight ratio of from about 1:2 to about 2:1.

* * * * *